United States Patent [19]
Kato

[11] Patent Number: 5,298,860
[45] Date of Patent: Mar. 29, 1994

[54] METHOD OF ANALYZING METAL IMPURITIES IN SURFACE OXIDE FILM OF SEMICONDUCTOR SUBSTRATE

[75] Inventor: Juri Kato, Suwa, Japan

[73] Assignee: Seiko Epson Corp., Tokyo, Japan

[21] Appl. No.: 796,823

[22] Filed: Nov. 25, 1991

[30] Foreign Application Priority Data

Nov. 26, 1990 [JP] Japan .................. 2-321763

[51] Int. Cl.$^5$ .............................. G01R 31/26
[52] U.S. Cl. .................. 324/158 R; 324/158 D
[58] Field of Search ........... 324/158 R, 158 D, 158 T, 324/719

[56] References Cited

U.S. PATENT DOCUMENTS

| | | | |
|---|---|---|---|
| 4,551,674 | 11/1985 | Miller | 324/158 D |
| 4,598,249 | 7/1986 | Goodman et al. | 324/158 R |
| 4,812,756 | 3/1989 | Curtis et al. | 324/158 D |
| 4,827,212 | 5/1989 | Kamieniecki | 324/158 R |

Primary Examiner—Ernest F. Karlsen
Attorney, Agent, or Firm—Oliff & Berridge

[57] ABSTRACT

A method of analyzing metal impurities in a surface oxide film of a semiconductor substrate enables a detection sensitivity of the order of $10^{11}$ atoms/cm$^2$ in a simple technique. This method comprises measuring a quantity of oxide charge resulting from specified metal impurities existing in the surface oxide film formed on the surface of a semiconductor substrate, and using a predetermined correlation between the quantity of metal impurities and the quantity of oxide charge to determine the quantity of metal impurities in the surface oxide film from the measured quantity of oxide charge of the surface oxide film. Further, it is possible to determine the distribution of concentration of the metal impurities in a thermal oxide film on a silicon substrate by determining a correlation between a depth of the thermal oxide film and a quantity of oxide charge resulting from the metal impurities in the thermal oxide film and by using the correlation between the quantity of the metal impurities in the thermal oxide film and the measured quantity of oxide charge resulting therefrom.

6 Claims, 6 Drawing Sheets

METHOD OF ANALYZING METAL IMPURITIES IN SURFACE OXIDE FILM OF SEMICONDUCTOR SUBSTRATE

BACKGROUND OF THE INVENTION

1. Field of the Invention

This invention relates to a method of analyzing metal impurities in an oxide film formed on the surface of a semiconductor substrate, and more particularly to a method of analyzing iron and aluminum impurity, which method is useful for quality control chiefly in the cleaning process during the production of LSI.

2. Description of the Related Art

The conventional means for analyzing metal impurities in the surface layer of a semiconductor substrate is exemplified by SIMS (Secondary Ion Mass Spectrometry) and TRXRF (Total Reflection X-ray Fluorescence).

However, these conventional analyzing methods requires a vacuum, which requires a large-sized and expensive analyzing apparatus. Therefore in the conventional methods, a simple analysis cannot be achieved.

SUMMARY OF THE INVENTION

It is therefore an object of this invention to provide a method of analyzing metal impurities in a surface oxide film of a semiconductor substrate, which method does not requires a vacuum, and therefore can be carried out in an inexpensive small-sized apparatus and which enables a detection sensitivity of the order of $10^{11}$ atoms/cm$^2$.

According to a first aspect of this invention, there is provided a method of analyzing metal impurities in a surface oxide film of a semiconductor substrate, comprising: measuring a quantity of oxide charge resulting from metal impurities existing in the surface oxide film formed on the semiconductor substrate; and using a correlation previously determined between the quantity of oxide charge and a quantity of the metal impurities to determine the quantity of metal impurities in the surface oxide film from the measured quantity of oxide charge in the surface oxide film.

According to a second aspect of the invention, there is provided a method of analyzing metal impurities in a surface oxide film of a semiconductor substrate, comprising: determining a correlation between a depth of a thermal oxide film formed on a silicon substrate and a quantity of oxide charge resulting from metal impurities in the thermal oxide film: determining a correlation between a quantity of metal impurities in the oxide film and the quantity of oxide charge resulting therefrom; and determining a distribution of concentration of the metal impurities in the thermal oxide film across said depth, based on the first and second correlations.

According to a third aspect of the invention, there is provided a method of analyzing metal impurities in a surface oxide film formed on a semiconductor substrate, wherein iron or aluminum in a natural oxide film is qualitatively analyzed by comparing a pre-measured quantity of oxide charge in the natural oxide film with measured quantity of oxide charge resulting from aluminum in a thermal oxide film formed on the natural oxide film and based on this comparison, determining how much iron and aluminum were contained in the natural oxide film.

A significant feature of the analyzing method of this invention is that the quality and quantity of the metal impurities can be analyzed by measuring the quantity of charge due to the metal impurities. The present inventor has discovered that specified metal impurities contained in the surface oxide film of a semiconductor substrate have a charge, and more particularly that iron in a natural oxide film has a negative charge and that when iron and aluminum in a natural oxide film are diffused into a thermal oxide film formed on the natural oxide film, only aluminum has a charge. This invention has been made based on these phenomena.

Thus a metal impurity which has a charge in an oxide film can be analyzed by the method of this invention. Such a specified metal impurity is exemplified by iron and aluminum. Copper and nickel do not have such characteristics. It has been discovered that in a natural oxide film both iron and aluminum have a charge and that in a thermal oxide film only aluminum has a charge.

In this specification, the term "natural oxide film" means an oxide film developed on an active silicon surface, for example, in atmosphere or a chemical oxide film formed, for example by RCA cleaning the latter example normally has a small thickness of about 10 Angstrom. The term "thermal oxide film" means an oxide film of about 100 Angstrom formed by oxidation in an oxygen gas at a high temperature of 800° to 1,200° C. in a furnace for oxidation.

In the first analyzing method of this invention, it is possible to determine the concentration of metal impurities by determining a quantity of oxide charge in a surface oxide film of the sampled substrate if a correlation is known between a quantity of metal impurities existing in either the surface oxide film (in the form of a natural oxide film or in) a thermal oxide film and the quantity of oxide charge resulting from the metal impurities.

In the second analyzing method, a quantity of oxide charge in a thermal oxide film formed on a silicon substrate is measured after a surface layer of the thermal oxide film has been removed, for examples, by etching. By repeating this process one or more times, it is possible to determine a correlation between the depth of the thermal oxide film and the quantity of oxide charge resulting from the metal impurities in the thermal oxide film as well as a correlation between the quantity of metal impurities in the thermal oxide film and the quantity of oxide charge resulting therefrom. Based on these correlations, it is possible to determine a correlation between the concentration of the metal impurities and the depth of the thermal oxide film, from which correlation the distribution of concentration of the metal impurities in the thermal oxide film can be determined Then the concentration of the metal impurity (aluminum) in the thermal oxide film can be determined by measuring the quantity of oxide charge in the thermal oxide film of the sampled substrate from the concentration distribution.

In the third analyzing method, the existence of iron or aluminum in a natural oxide film can be directed by comparing a pre-measured quantity of oxide charge in the natural oxide film with a premeasured quantity of oxide charge resulting from aluminum in the thermal oxide film, based on the fact that when iron and aluminum move from the natural oxide film into the thermal oxide film, only aluminum has a charge.

As described above, according to the analyzing method of this invention, it is possible to specify the type of a metal impurity in the surface oxide film and to detect the concentration of the metal impurity with high precision by simply measuring the quantity of oxide charge in the surface oxide film.

DETAILED DESCRIPTION

Embodiments of this invention will now be described in detail with reference to the accompanying drawings.

Figure 1:
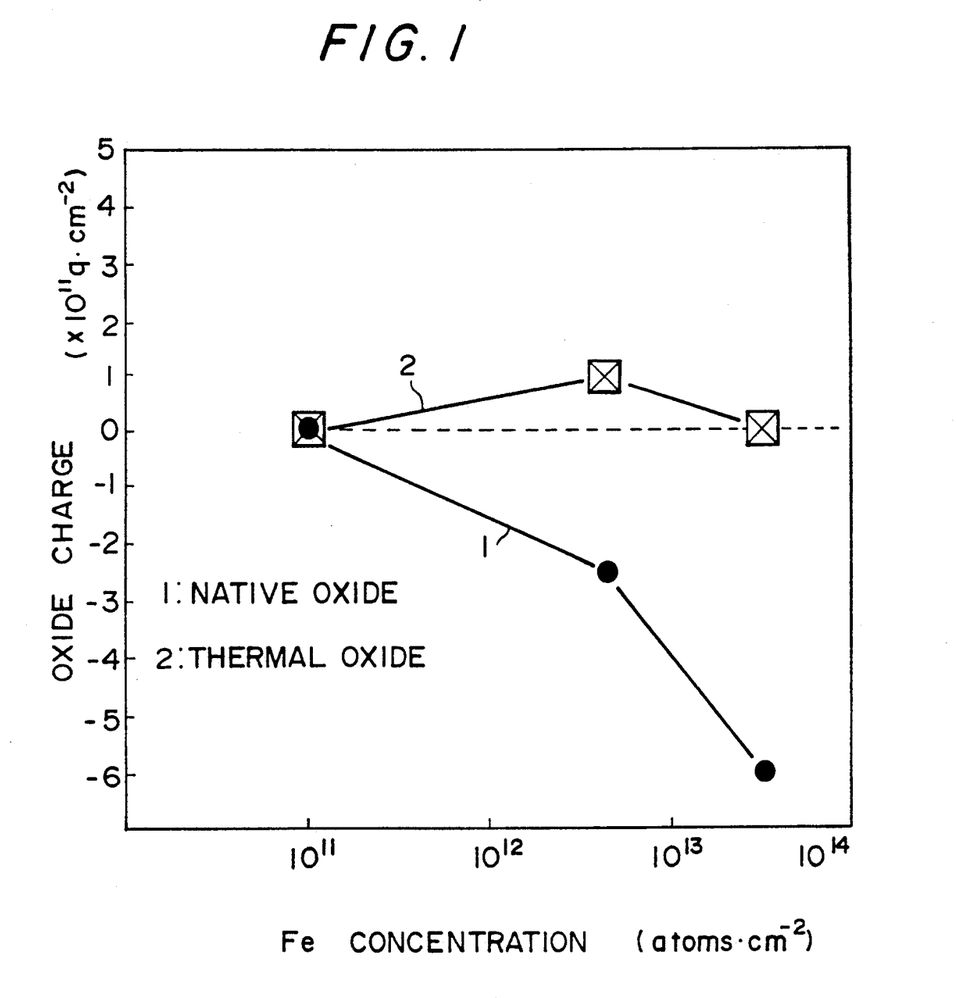
FIG. 1 is a characteristic graph showing the correlation between the Fe concentration and the quantity of oxide charge in a natural oxide film or in a thermal oxide film.

FIG. 1 shows the correlation (curve 1) between the iron (Fe) impurity concentration (atoms/cm$^2$) and the quantity of oxide charge ($\times 10^{11}$q/cm$^2$) in a natural (native) oxide film formed on the surface of a silicon substrate, and also shows the correlation (curve 2) between the Fe impurity concentration (atoms/cm$^2$) and the quantity of oxide charge ($\times 10^{11}$q/cm$^2$) in a thermal oxide film.

For obtaining the correlation shown by the curve 1, as a pre-treatment process, the surface of an n-type silicon substrate is wet-cleaned by a first cleaning process (hereinafter called "SC-1"), which is performed in the following order:

(a) etching with an HF cleaning solution (HF:water=1:10) for three minutes.
(b) rinsing with pure water for three minutes.
(c) cleaning with an oxide agent (HCl:H$_2$O$_2$:-water=1:1:6) at 60° C. for three minutes.
(d) rinsing with pure water for three minutes.

By the wet-cleaning of the first cleaning process, a natural oxide film (chemical oxide film) of about 10 Angstrom is formed on the silicon substrate. An oxide agent containing HCl is useful in removing metal impurities on the substrate.

Then, the surface of the natural oxide film is coated with an Fe solution by rotating the substrate while dropping onto the surface of the substrate an Fe solution containing Fe ions in a predetermined concentration, namely, by the spin-coat method, whereupon the natural oxide film is dried. The resulting sample contains Fe in the natural oxide film by a predetermined concentration. In this experiment, as shown in FIG. 1, for three types of samples of different Fe concentrations, a concentration of Fe and a quantity of oxide charge resulting from Fe in the natural oxide film are obtained. The more points of measurement, the more precise the impurities-oxide charge correlation curve can be obtained.

Subsequently, Fe in the natural oxide film is perfectly dissolved in a clean HF solution (HF:water=1:200) containing neither Fe ions nor Al ions by etching the natural oxide film with the HF solution, and this solution is collected, whereupon the quantity of Fe impurities in the natural oxide film is measured by atomic absorption.

The quantity of oxide charge in the natural oxide film is obtained by measuring the relation (C-V) between a D.C. bias voltage V and a depletion layer capacitance C by measuring the surface photoelectric voltage (SPV) generated by applied LED intermittent light to the surface in proportion to the width of a semiconductor depletion layer while varying the D.C. bias voltage. In the C-V measurement of this SPV method, the inversion voltage (initially a positive d.c. bias voltage is applied to an n-type silicon substrate) is adopted. The SPV method is disclosed in a publication: E. Kamieniecki. SEMICON/EUROPA 91 TECHNICAL PROCEEDINGS, pages 85-95, Mar. 5-6 (1991).

As is apparent from the curve 1 of FIG. 1, along with the increase of the quantity of Fe impurities in the natural oxide film on the silicon substrate, the quantity of negative charge in the natural oxide film was increased. Thus it was observed that Fe would have a negative charge when incorporated in a natural oxide film.

Further, according to this measuring method, measurement of charge is possible even if the quantity of Fe is around 10$^{11}$ atoms/cm$^2$. Thus it was observed that Fe in a natural oxide film on a silicon substrate surface could be detected in the order of 10$^{11}$ atoms/cm$^2$ from the C-V analysis using the SPV method.

The correlation, which is represented by the curve 2, between the Fe concentration and the quantity of oxide charge in the thermal oxide film was obtained by the following method.

A natural oxide film contaminated with Fe was formed in the same manner as the sample formed to obtain the above-mentioned curve 1, and a thermal oxide film was formed on the natural oxide film. This thermal film was formed by heating the substrate in an atmosphere of oxygen gas at 900° C. for 15 minutes, and had a thickness of about 95 Angstrom. Then, the Fe concentration and the quantity of oxide charge in the thermal oxide film were obtained using the abovementioned method.

As is apparent from the curve 2 of FIG. 1, it was observed that in the thermal oxide film, Fe has almost no negative charge, irrespective of its concentration.

Figure 2:
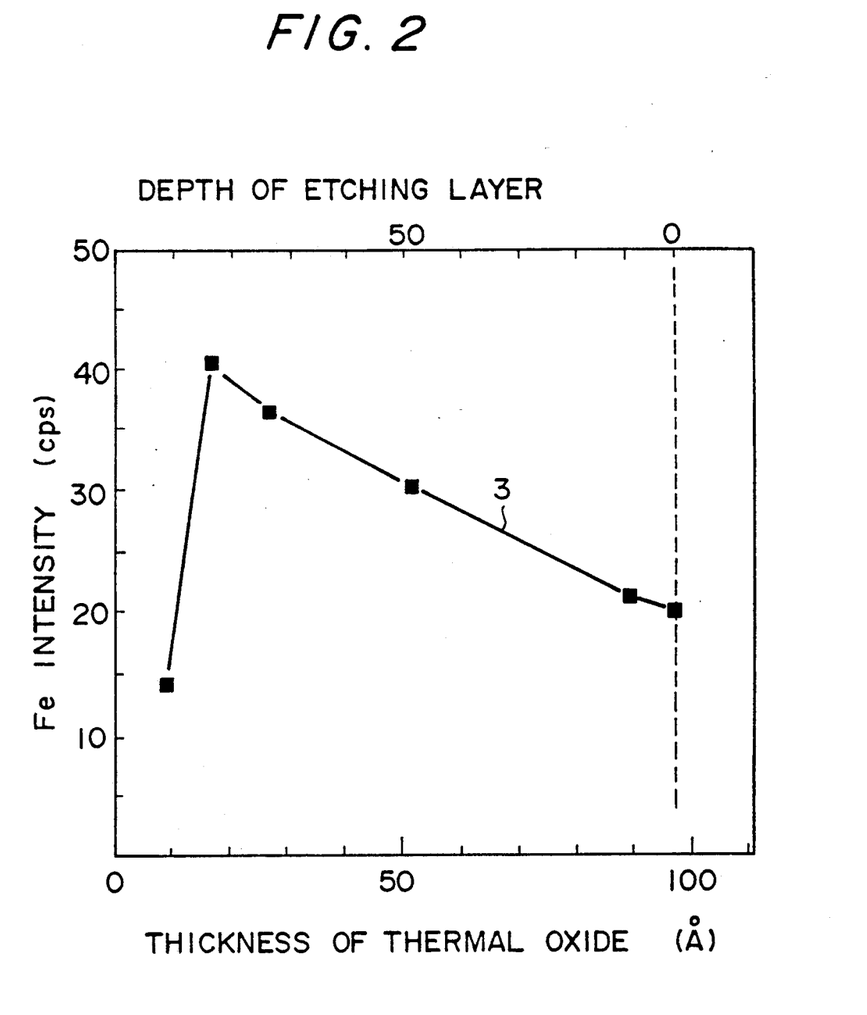
FIG. 2 is a graph showing the distribution of Fe in the depthwise direction of the thermal oxide film.

FIG. 2 shows the distribution of Fe in the depthwise direction of the thermal oxide film. This distribution was obtained in the following manner.

The sample used in this test is a thermal oxide film (thickness: about 95 Angstrom) formed by dry oxidation at 900° C. for 15 minutes after cleaning a silicon substrate by the first cleaning method and then doping Fe into the substrate in the concentration of $1 \times 10^{14}$ atoms/cm$^2$ by the spin coat method.

Using this sample, the concentration of Fe at two or more positions in the depthwise direction of the thermal oxide film was obtained by the TRXRF method. More specifically, first the concentration of FE at the surface of the thermal oxide film was obtained by the TRXRF method. Subsequently, the thermal oxide film was etched with an HF solution, and the surface layer of the thermal oxide film was removed, whereupon the concentration of Fe was measured. By repeating this procedures, the distribution of Fe in the thermal oxide film was obtained.

As is apparent from the curve 3, it was observed that the number of Fe atoms in the thermal oxide film increased along with the increase of depth of the thermal oxide film, peaking and localizing near the border of the thermal oxide film and the silicon substrate.

From the curves 2 and 3, it was observed that Fe in the thermal oxide film localized near the silicon substrate and had no negative charge.

Figure 3:
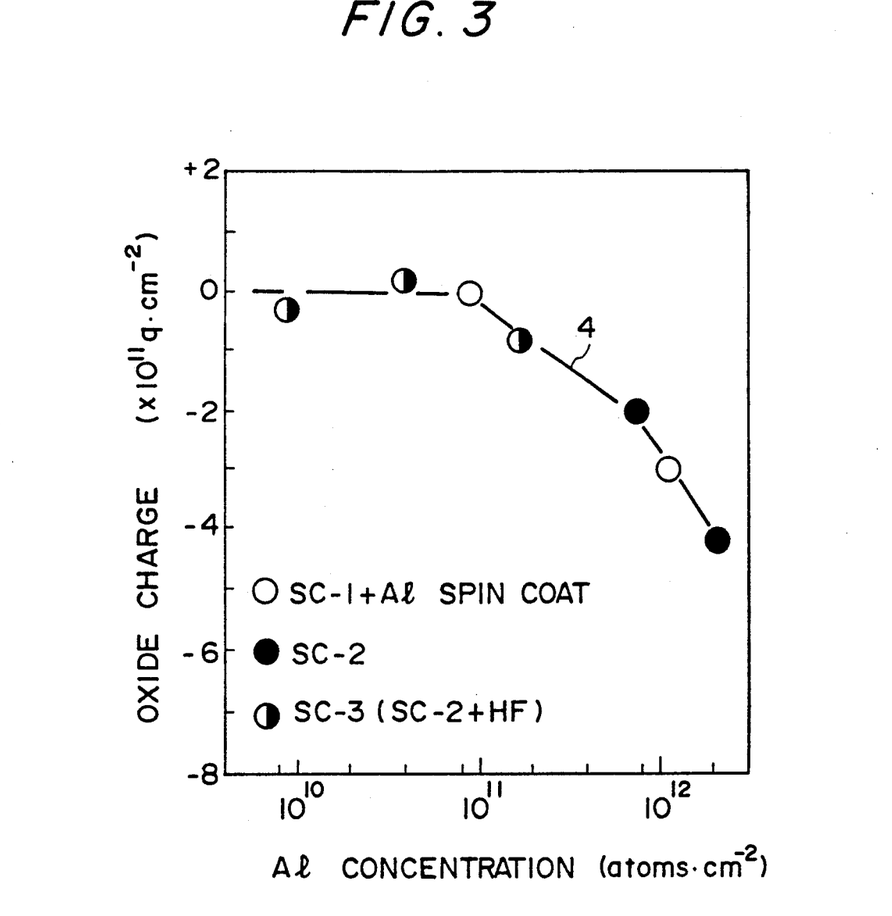
FIG. 3 is a characteristic graph showing the correlation between the Al concentration and the quantity of oxide charge when a thermal oxide film is formed on a natural oxide film.

FIG. 3 shows the correlation between the Al concentration and the quantity of oxide charge in the thermal oxide film.

The pre-treatment process to be used in this test for the silicon substrate is exemplified by the following:
(a) doping, onto the substrate wet-cleaned by the first cleaning method. Al atoms by the spin coat method (SC-1+Al spin coat).
(b) wet cleaning by the second cleaning method (SC-2) using the following solutions in the described order:
  1) HF:water (1:10) for three minutes.
  2) rinsing with pure water for three minutes.
  3) $NH_4OH:H_2O_2$:WATER (1:1:6) at 60° C. for three minutes.
  4) rinsing with pure water for three minutes.
(c) wet cleaning by the third cleaning method (SC-3) using the following solutions in the described order:
  1) HF:water (1:10) for three minutes.
  2) rinsing with pure water for three minutes.
  3) $NH_4OH:H_2O_2$:water (1:1:6) at 60° C. for three minutes.
  4) HF:water (1:300) for one to two minutes.

The correlation curve 4 of FIG. 3 was obtained using the following procedures:

A silicon substrate underwent one of the foregoing pre-treatment processes including wet cleaning. By this pre-treatment process, a natural oxide film was formed on the silicon substrate by chemical oxidation.

Then a thermal oxide film having a thickness of about 95 Angstrom was formed by dry oxidation at 900° C. for 15 minutes.

Subsequently, the quantity of oxide charge of this thermal oxide film was obtained by the SPV method, and the Al concentration, similar to the Fe concentration, in the thermal oxide film was obtained by atomic absorption.

By plotting the thus obtained values of each sample in FIG. 3, the curve 4 representing the correlation between the Al concentration and the quantity of oxide charge in the thermal oxide film was obtained.

The result represented by the curve 4 shows that Al existing in the natural oxide film had a negative charge when incorporated into the thermal oxide film and that when the Al concentration was larger than $10^{11}$ atoms/cm$^2$, the negative charge increased substantially linearly along with the increase of concentration.

When the second cleaning method (SC-2) and the third cleaning method (SC-3) were performed as the pre-treatment process as well as when Al was positively doped into the natural oxide film (SC-1+Al spin coat), it was also observed that Al was contained as impurities in the natural oxide film and was diffused into the thermal oxide film. In this test, in the case of the second cleaning method (SC-2), the concentration of Al impurities was high.

Figure 4:
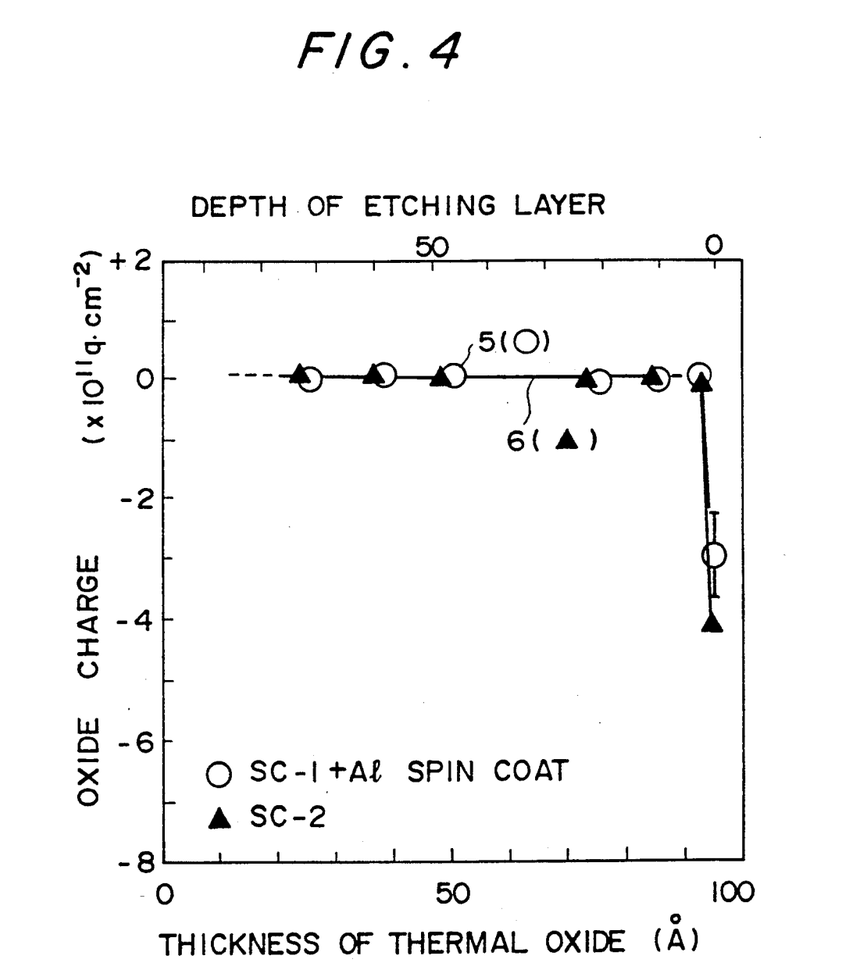
FIG. 4 is a graph showing the distribution of quantity of oxide charge of Al in the depthwise direction of the thermal oxide film.

FIG. 4 shows the correlation between the thickness (depth of etching) of the thermal oxide film and the quantity of oxide charge, illustrating the distribution of Al in the depthwise direction of the thermal oxide film.

The samples used in this test were a substrate whose surface was contaminated the Al concentration of about $1 \times 10^{12}$ atoms/cm$^2$ after performing the first cleaning method as the pre-treatment process (SC-1+Al spin coat) and a substrate whose surface was treated by the second cleaning (SC-2) method as the pre-treatment process.

Figure 5:
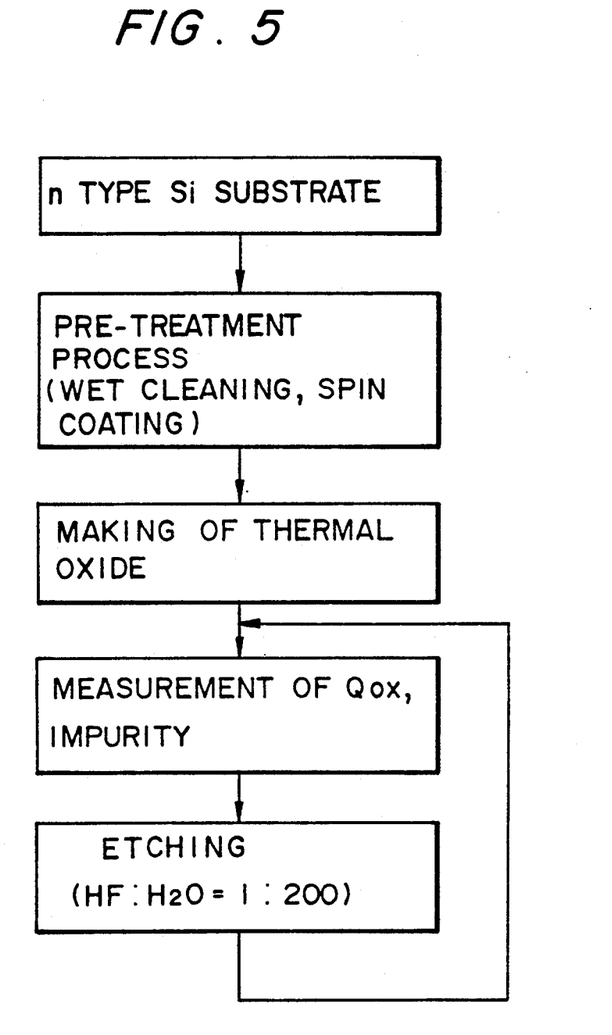
FIG. 5 is a flow diagram showing the forming and measuring of a sample for obtaining the correlation diagram of FIG. 4.

The correlation curves 5 and 6 of FIG. 4 were obtained according to the flow diagram of FIG. 5. After an n-type silicon substrate was treated with the foregoing pre-treatment processes, dry oxidation was performed at 90° C. for 15 minutes to form a thermal oxide film. Then, the quantity of oxide charge and the Al concentration in this thermal oxide film were measured by the above-mentioned method. Subsequently, the surface layer (about 2 Angstrom) of the thermal oxide film was removed by etching using an HF solution, whereupon the quantity of oxide charge and the Al concentration in the resulting thermal oxide film were measured again. The foregoing etching and measuring processes were repeated one or more times.

Thus it was observed that the correlation curve 5 (according to SC-1+Al spin coat) and the correlation curve 6 (according to SC-2) were substantially identical with each other. As is apparent from these correlation curves 5 and 6, almost all of the negative charge resulting from Al localized at the region of 2 Angstrom from the top surface of the thermal oxide film. Thus it was observed that part of the Al existing in the natural oxide film (i.e., chemical oxide film) formed by the foregoing pre-treatment process was diffused and moved toward the surface of the thermal oxide film after thermal oxidation.

Figure 6:
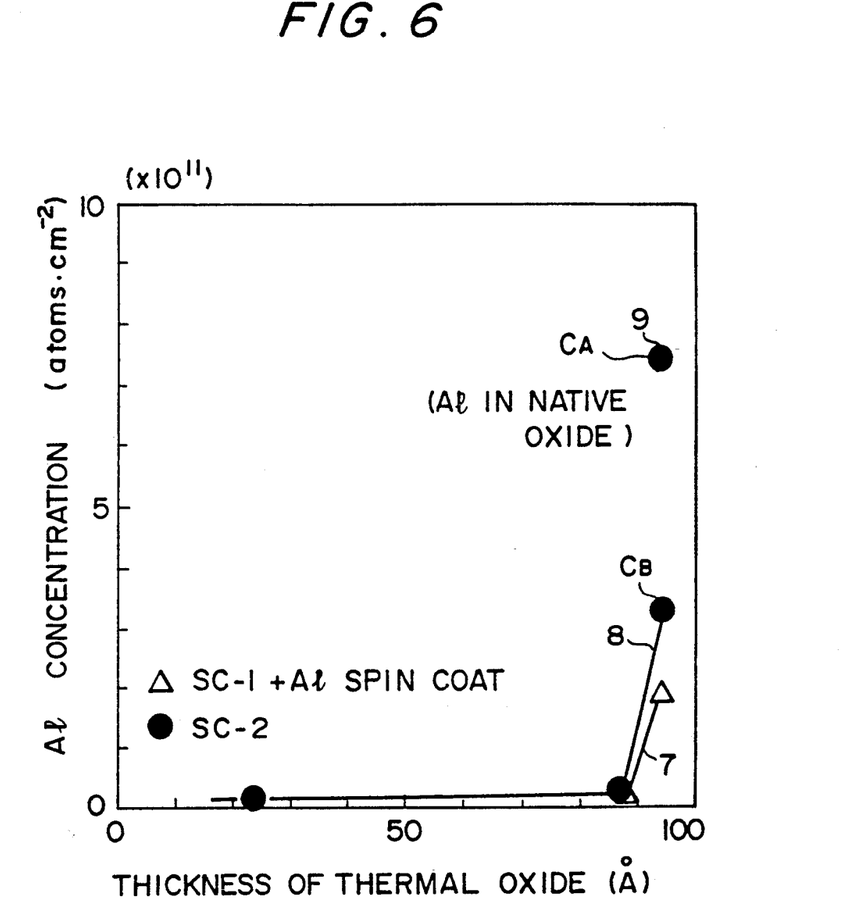
FIG. 6 is a graph showing the distribution of Al concentration in the depthwise direction of the thermal oxide film.

FIG. 6 shows the correlation between the thickness (depth) and the Al concentration in the thermal oxide film. In this test, two types of samples treated by SC-1+Al spin coat and SC-2 as pretreatment processes were used.

The measuring method used in this test was as follows: The samples treated by the different pre-treatment processes were formed under the same conditions; the number of samples of each type was equal to the number of points of measurement. For SC-2, a separate sample substrate which would have only a natural oxide film and would be devoid of any thermal oxide film should be formed in advance.

Then, regarding each of the samples different in thickness, the Al concentration in the individual thermal oxide film was measured. Describing this more specifically using SC-1+Al spin coat by way of illustrative example, the Al concentration in the thermal oxide film of one sample substrate was measured by atomic absorption. Then using another sample substrate, the surface portion of the thermal oxide film having a thickness of about 6 Angstrom was removed by etching with an HF solution, and the Al concentration of the remaining thermal oxide film was measured. By plotting the thus obtained result in FIG. 6, the correlation curve 7 was obtained.

Likewise, the correlation curve 8 was obtained by plotting the result of measurement for SC-2. A plot 9 was obtained by measuring the Al concentration in the natural oxide film treated by SC-2.

As is apparent from the correlation curves 7 and 8 of FIG. 6, it was observed that Al existing in the natural oxide film was moved into the thermal oxide film to localize very near the top surface, proving the result shown in FIG. 4. When the cleaning process (SC-2) was used as a pre-treatment process, Al impurities were incorporated in the natural oxide film and subsequently contaminated the thermal oxide film. In the case of SC-2, about 40% (concentration $C_B$) of Al (concentration $C_A$) existing into the natural oxide film was incorporated in the thermal oxide film.

In the thermal oxide film, Fe had no charge. From the result shown in FIGS. 4 and 6, it was observed that the quantity of oxide charge in the thermal oxide film resulted from Al impurities and that the Al impurities localized at the very surface layer of the thermal oxide film. Thus the quantity of oxide charge resulting from Al can be determined by the difference $Q_C$ between the quantity of oxide charge $Q_A$ when the etching depth was zero and when the depth of the thermal oxide film was zero, and the quantity of oxide charge $Q_B$ when the very surface layer (layer having a depth of about 2 to 6 Angstrom) was removed. Therefore, the Al concentration in the thermal oxide film can be obtained from the differential quantity of oxide charge $Q_C$, based on the Al concentration-oxide charge correlation curve of FIG. 3.

Further, by pre-measuring (i.e., prior to forming the thermal oxide film) the quantity of oxide charge in the natural oxide film formed by the pretreatment process (wet cleaning) and then comparing this quantity of oxide charge with the quantity of oxide charge in the thermal oxide film, it is possible to qualitatively analyze Fe and Al in the natural oxide film. In other words, though both Fe and Al are moved from the natural oxide film into the thermal oxide film, only Al has a charge in the thermal oxide film. Therefore, if an oxide charge is detected in the thermal oxide film, it shows that Al is contained in the natural oxide film. By pre-detecting the portion of Al initially existing in the natural oxide film which will be moved to the thermal oxide film, it is possible to estimate the approximate concentration of Al (i.e., the quantity of Al oxide charge) in the natural oxide film. By comparing this quantity of Al oxide charge with the total quantity of oxide charge in the natural oxide film, it is possible to presume the presence/absence and the approximate quantity of Fe in the natural oxide film.

According to this invention, the following quantitative and qualitative analyses can be realized:

(1) It is possible to obtain the concentration of the total amount of Fe and Al in a natural oxide formed on a silicon substrate.

(2) By forming a thermal oxide film on the natural oxide film, it is possible to measure the concentration of Al moved from the natural oxide film into the thermal oxide film.

(3) By evaluating the concentration of total amount of Fe and Al in the natural oxide film of determined by (1) above and the concentration determined by Al in the thermal oxide film of (2) above, it is possible to detect the presence of Fe and Al in the natural oxide film and also to presume their ratio.

According to this invention, it is possible to detect Al atoms and Fe atoms, in the order of $10^{11}$ atoms/cm$^2$, which are highly apt to cause contamination in various cleaning processes, such as RCA cleaning, in the LSI manufacturing process. Since the SPV method is used in the analyzing method, it is possible to carry out this invention easily and inexpensively on a small-sized apparatus.

Regarding Ni and Cu atoms of metal impurities, because no oxide charge would be generated in a silicon oxide film, they cannot be detected by the analyzing method of this invention.

What is claimed is:

1. A method of analyzing metal impurity in a surface oxide film of a semiconductor substrate, comprising:
   (a) applying a d.c. bias voltage V to the semiconductor substrate;
   (b) applying LED intermittent light to the surface oxide film in proportion to the width of a semiconductor depletion layer while varying the d.c. bias voltage V applied to the semiconductor substrate;
   (c) determining a quantity of oxide charge resulting from a metal impurity of at least one of iron and aluminum existing in the surface oxide film formed on the semiconductor substrate based on a relation between said d.c. bias voltage V applied to the semiconductor substrate and a depletion layer capacitance C determined by detecting a surface photoelectric voltage generated when said LED intermittent light is applied to said surface oxide film; and
   (d) using a predetermined correlation between the quantity of oxide charge and a quantity of the metal impurity to determine the quantity of metal impurity of at least one of iron and aluminum in the surface oxide film from the measured quantity of oxide charge in the surface oxide film.

2. An analyzing method according to claim 1, wherein the surface oxide film to be analyzed is a natural oxide film.

3. An analyzing method according to claim 1, wherein said predetermined correlation is determined by measuring a quantity of oxide charge in a sample surface oxide film, and then measuring the quantity of metal impurity in the sample surface oxide film corresponding to the measured oxide charge by using atomic absorption after the surface oxide film has been dissolved in a clean hydrogen fluoride solution devoid of metal impurity and the metal impurity collected.

4. An analyzing method according to claim 1, wherein the surface oxide film to be analyzed is a thermal oxide film.

5. An analyzing method according to claim 2, wherein the metal impurity is iron and aluminum.

6. An analyzing method according to claim 4, wherein the metal impurity is aluminum.

* * * * *